United States Patent [19]
Taramasso et al.

[11] Patent Number: 4,656,016
[45] Date of Patent: Apr. 7, 1987

[54] SILICA-BASED SYNTHETIC MATERIALS CONTAINING BORON IN THE CRYSTAL LATTICE AND PROCESSES FOR THEIR PREPARATION

[75] Inventors: Marco Taramasso; Giovanni Manara; Vittorio Fattore; Bruno Notari, all of San Donato Milanese, Italy

[73] Assignee: Snamprogetti, S.p.A., Milan, Italy

[21] Appl. No.: 662,523

[22] Filed: Oct. 18, 1984

Related U.S. Application Data

[63] Continuation of Ser. No. 535,361, Sep. 23, 1983, abandoned, which is a continuation of Ser. No. 258,716, Apr. 27, 1981, abandoned, which is a continuation of Ser. No. 46,923, Jun. 8, 1979, abandoned.

[30] Foreign Application Priority Data

Jun. 22, 1978 [IT] Italy ............................... 22844 A/78
May 14, 1979 [IT] Italy ............................... 22638 A/79

[51] Int. Cl.4 .............................................. C01B 33/28
[52] U.S. Cl. .................................... 423/277; 423/326; 423/328; 423/329; 502/60; 502/62; 502/77; 502/79; 502/202
[58] Field of Search ....................... 423/277, 326–333, 423/335; 502/60, 77, 202, 214

[56] References Cited

U.S. PATENT DOCUMENTS

| 3,308,069 | 3/1967 | Wadlinger et al. | 423/328 X |
| 3,702,886 | 11/1972 | Argauer et al. | 423/328 |
| 3,709,979 | 1/1973 | Chu | 423/328 |
| 3,941,871 | 3/1976 | Dwyer et al. | 423/326 |
| 3,972,983 | 8/1976 | Ciric | 260/448 C |
| 4,060,590 | 11/1977 | Whittam et al. | 423/328 |
| 4,071,377 | 1/1978 | Schwuger et al. | 423/329 X |
| 4,104,294 | 8/1978 | Grose et al. | 260/448 C |
| 4,269,813 | 5/1981 | Klotz | 423/277 |
| 4,410,501 | 10/1983 | Taramasso et al. | 423/326 |

OTHER PUBLICATIONS

Civil Action 83-207 Mobil Oil Corp. Amoco Chemicals Corp. District Court Delaware.
Civil Action 85-102 (LON) Union Carbide Corp. Mobil Oil Corp. District Court Delaware.
Taramasso et al. "Proceedings of the Fifth International Conference on Zeolites" Jun. 1980, pp. 1-8.

Primary Examiner—John Doll
Assistant Examiner—Jackson Leeds
Attorney, Agent, or Firm—Hedman, Gibson, Costigan & Hoare

[57] ABSTRACT

The invention is concerned with particular crystalline silica materials that contain boron in the crystal lattice. These materials are useful as catalysts for many reactions.

7 Claims, 4 Drawing Figures

SILICA-BASED SYNTHETIC MATERIALS CONTAINING BORON IN THE CRYSTAL LATTICE AND PROCESSES FOR THEIR PREPARATION

This is a continuation of application Ser. No. 535,361 filed Sept. 23, 1983, abandoned, which is a continuation of application Ser. No. 258,716 filed Apr. 27, 1981, abandoned, which in turn is a continuation of Ser. No. 046,923 filed June 8, 1979, now abandoned.

This invention relates to silica-based synthetic materials. More particularly, the invention has as its subject matter a novel synthetic material which is composed by a modified crystalline silica which has a high specific surface area and relates also to the method for its preparation and the processes in which said novel material can be exploited.

More detailedly novel types of materials are considered, to be called briefly TRS hereinafter and which are composed by silicas modified by elements which can enter into the crystalline lattice both as substituents for silicon and as salts of polysilicic acids, consistently with the nature and the relative amounts of the reactants.

As elements which can be used for obtaining the modified silicas referred to above, all the metallic cations can be indicated, but special preference is accorded, were it only to simplify the procedure, to elements having, at least partially, an amphoteric character, such as chromium, beryllium, titanium, vanadium, manganese, iron, cobalt, zinc, zirconium, rhodium, silver, tin, antimony and boron.

Modified silicas of this kind are characterized by the presence of a single crystalline phase and can exist within the following molar ratios, i.e. from 0.0001 to $1M_nO_m \cdot 1SiO_2$, wherein $M_nO_m$ is the oxide of one or more of the metals listed above.

The product can contain small amounts of water, the quantity being greater or smaller consistently with the calcination temperature. The materials according to the present invention possess a very high thermal stability and are characterized by their composition, the preparation procedures and the crystalline structures, all to be described and exemplified hereinafter, and by their high specific surface areas, as well as by acidity due to Lewis' systems, by acidity due to Brønsted systems, these being adjustable according to the nature of the cation which has been introduced as the modifying agent.

A wide variety is known of amorphous silicas having a high or a low specific surface area, such as they can be obtained with the well known procedures of gelling of silica-sols or also by precipitation and gelling of various silicates (U.S. Pat. Nos. 2,715,060, 3,210,273, 3,236,594, 3,709,833).

More recently, U.S. Pat. No. 3,983,055 has claimed a synthetic amorphous silica having a preselected pore distribution and the method for its preparation, which consists in the hydrolysis of an organic derivative of silicon and the condensation by polymerization, and calcination. A number of crystalline types of silica are known, such as quartz, crystobalite, tridymite, keatite and many others, prepared according to procedures which have widely been described by the technical literature. For example, Heidemann, in Beitro Min. Petrog. 10, 242 (1964), obtains, by reacting at 180° C. an amorphous silica with 0.55% of KOH, in two days and a half, a crystalline silica, called silica-X, which has a specific surface area of about 10 m²:g (square meters per gram) and has a poor stability since, within five days, it is converted into cristobalite and then into quartz. Recently, Flanigen et al., Nature, 271,512 (1978) have obtained a crystalline silica, silicalite, having a high specific surface area and, on account of its hydrophobic nature, have suggested its use for the purification of waters polluted by organic substances.

An object of the present invention is to modify the nature of a crystalline silica by leaving its stability unaltered, to enable it to be used as a catalyst, or for the preparation of catalysts.

Catalytic properties can be imparted, for example, by endowing crystalline silica with acidic properties.

Another object of the present invention is to provide a procedure for the preparation of crystalline modified silicas endowed with such properties.

Figure 1:
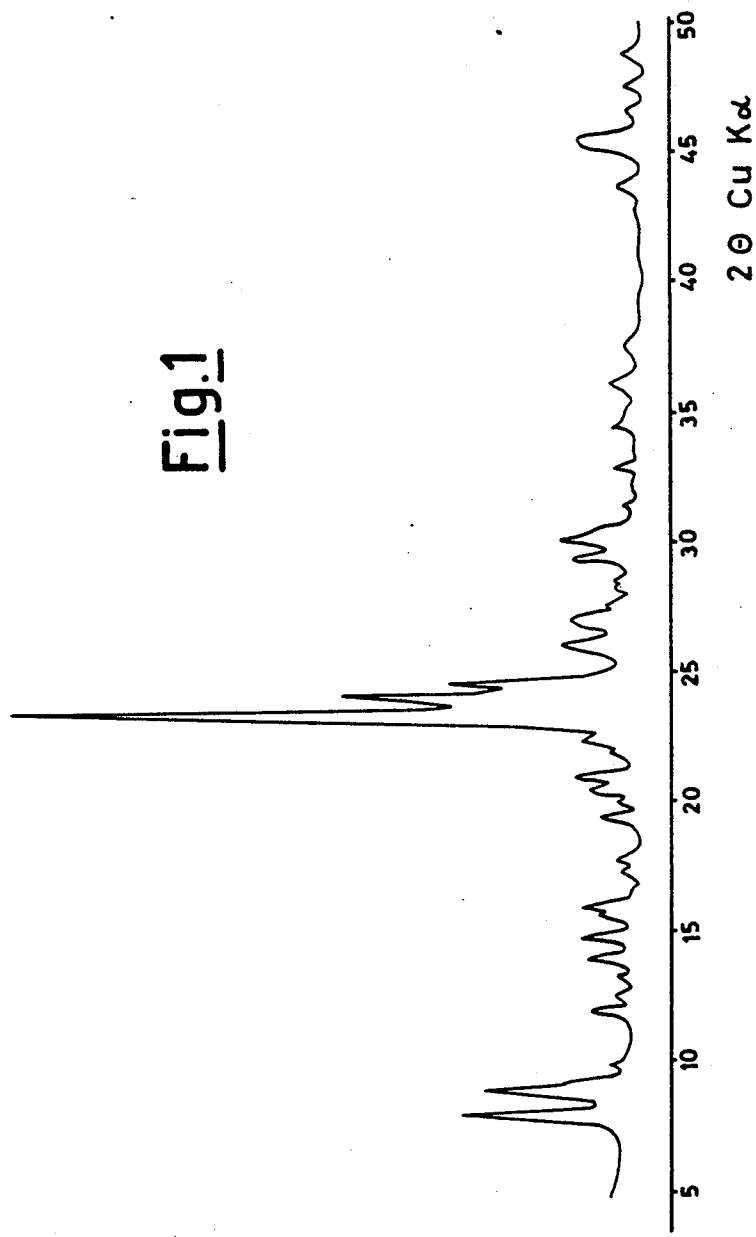
FIG. 1 is an X-ray powder diffraction spectrum of the product of Example 1.
Figure 2:
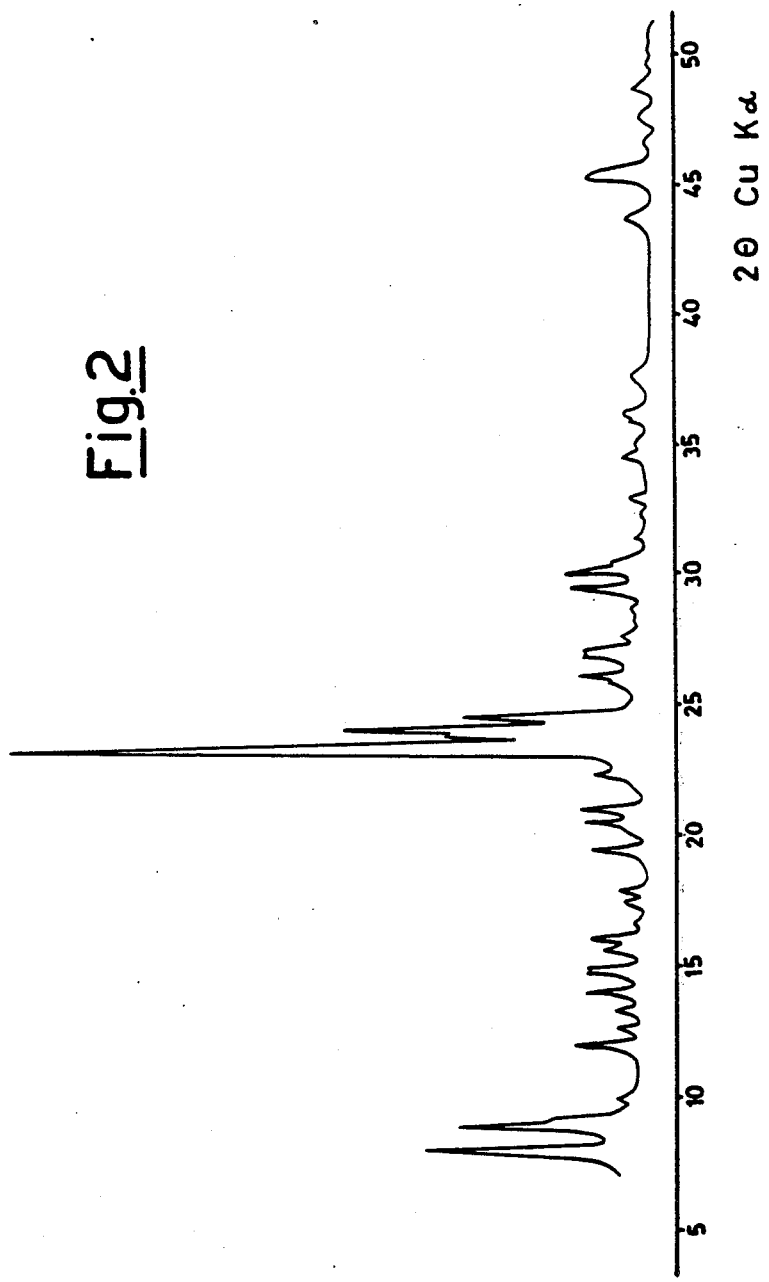
FIG. 2 is an X-ray powder diffraction spectrum of the product of Example 2.

Whereas the modifying element has a predominant bearing on the catalytic properties of silica, the addition of such element originates the formation of crystalline materials the spectra of which can either be closely similar to the silicalite spectrum, or sharply different, as shown in FIGS. 1 and 2 of the accompanying drawings.

The TRS silicas, modified by addition of elements which are the subjectmatter of the present invention, are characterized by their crystalline structure and can exist with the molar ratios of the general formula 0.0001 to $1M_nO_m \cdot 1SiO_2$, wherein $M_nO_m$ is the oxide of a metallic cation capable of entering into the crystalline lattice of silica as a replacement of silicon, or also as a salt of silicic or polysilicic acids. According to the calcination temperature, greater or smaller quantities of water can be present.

All the metallic cations are useful for the obtention of the modified silicas according to the present invention, but elements are preferred, which have an amphoteric nature, even only partially, such as chromium, beryllium, titanium, vanadium, manganese, iron, cobalt, zinc, zirconium, rhodium, silver, tin, antimony and boron.

In order that the synthetic material according to the present invention may be obtained, the preparation procedure specified hereinafter can be adopted with advantage.

A derivative of silicon is caused to be reacted, in an aqueous, alcoholic or hydroalcoholic solution, with a derivative of a modifying element and a substance having an archivolt or clathrate-forming effect, possibly adding one or more mineralizing agents to encourage crystallization, and possibly also by adding an inorganic base. Crystallization of the mixture is caused to take place in a closed environment for a period ranging from a few hours to several days at a temperature of from 100° C. to 220° C., preferably between 150° C. and 200° C. for a week. Thereafter, cooling is effected and thus washing and collection on a filter are carried out. Calcination in air between 300° C. and 700° C., preferably at 550° C., is carried out for a time variable from 2 hrs and 24 hours. Washing is performed to remove the possible exchangeable cationic impurities, possibly with boiling dist. water containing, dissolved therein, an ammonium salt, preferably a nitrate or an acetate, and firing is then repeated as specified hereinabove.

The derivatives of silicon can be selected from among a silica-gel (no matter how it has been obtained) or a tetraalkyl orthosilicate, such as tetraethyl orthosilicate and tetramethyl orthosilicate.

The derivatives of the modifying element are selected from among the oxides, hydroxides, salts of alcoxy derivatives of the elements aforementioned. The preferred salts are, more particularly, the nitrates and the acetates.

The substances which display an archivolt or clathrate-forming effect can be selected from among the tertiary amines, the aminoalcohols, the aminoacids, the polyalcohols and the quaternary-ammonium bases such as tetraalkylammonium bases ($NR_4OH$) wherein R is a $C_1$ to $C_5$ alkyl, or tetrarylammonium ($NA_4OH$) base wherein A is a phenyl or an alkylphenyl radical.

The clathrating substances have the task of providing a crystalline structure having pores of well determined size, and thus such substances are composed by comparatively big molecules.

The mineralizing agents can be selected from among the alkali metal- or alkaline earth-hydroxides or halides, such as, for example, $LiOH$, $NaOH$, $KOH$, $Ca(OH)_2$, $KBr$, $NaBr$, $NaI$, $CaI_2$, $CaBr_2$.

The added inorganic base can be selected from among the alkali metal- or the alkaline earth metalhydroxides, preferably $NaOH$, $KOH$, $Ca(OH)_2$ and ammonia.

As regards the amounts of inorganic base and/or of clathasting substances to be used, these are, as a rule, lower than the stoichiometric amount relative to silica and are preferably from 0.05 mol% to 0.50 mol% per mol of silica.

The products which are so obtained are characterized by a protonic-type acidity, which can be monitored by varying the substituting cation which is introduced. For a pure silica there is a number of milliequivalents of hydrogen ions of $1.10^{-3}$ per gram of sample: this acidity can be increased by introducing the substituting element in such an amount that the number of millequivalents of hydrogen ions per gram of sample may reach roughly $5.10^{-1}$ meqH+.

For effecting particular catalytic reactions, it may prove appropriate to reduce the acidity by introducing alkalies until reaching neutrality or even basicity.

The materials obtained with the present invention are characterized by a well defined crystalline structure, such as can be seen in the X-ray diffraction spectra reported on FIGS. 1 and 2 of the accompanying drawings and possess a high specific surface area which exceeds 150 g/m² and is comprised, as a rule, between 200 m²/g and 500 m²/g. In addition, the materials according to the present invention are characterized by a porous structure exhibiting a pore size predominantly comprised between 4 and 7 Å units in diameter. To the crystalline silica which has been so prepared, which contains a cation which is either a replacement for silicon or is capable of forming with silicon a salt of polysilicic acids, other metals can be added which are capable of imparting special catalytic properties. Among such metals, the following can be listed by way of mere examples: platinum, palladium, nickel, cobalt, tungsten, copper, zinc and others. This addition can be effected by impregnation or any other method known to those skilled in the art by adopting solutions of salts of the selected metals such as, preferably, nitrates, acetates, or oxide and other compounds.

Consistently with the added metal(s), the catalytic properties can be imparted to silica or can they be improved, for example with the aim of carrying out hydrogenations, hydrations, hydrosulphurizations, crackings, reformings, oxidations, isomerizations, disproportionations, polymerizations and otherwise.

The silica-based materials prepared as described herein can be used for catalytic reactions or absorptions as such or also dispersed on a supporting body, more or less inert, having a high or a low specific surface area and porosity.

The supporting body has the task of improving the physical stability and the mechanical resistance and, possibly, the catalytic properties of the material, if any.

The procedure to be adopted for obtaining the supported active material can be selected from among those known to those skilled in the art.

The quantity of modified silica can be comprised between 1% and 90% but amounts of from 5% to 60% are preferred.

Among the preferred supporting bodies, examples are clays, silica, alumina, diatomaceous earths, silica-alumina and others.

The silica-based synthetic material according to the present invention, can profitably be employed as a catalyst for a huge number of reactions: among these, alkylation of benzene, especially the alkylation of benzene with ethylene and the alkylation of benzene with ethanol, can be indicated.

Other possible uses are:
1. Alkylation of toluene with methanol to produce xylene, predominantly para-xylene.
2. Disproportionation of toluene to produce para-xylene prevailingly.
3. Conversions of dimethyl ether and/or methanol or other alcohols (lower) into hydrocarbons such as olefins and aromatics.
4. Cracking and hydrocracking.
5. Isomerization of non paraffins and naphthenes.
6. Polymerization of compounds which contain olefin or acetylene bonds.
7. Reforming.
8. Isomerization of polyalkyl-substituted aromatics, such as ortho-xylene.
9. Disproportionation of aromatics, especially of toluene.
10. Conversion of aliphatic carbonyl compounds into at least partially aromatic hydrocarbons.
11. Separation of ethylbenzene from other C8 aromatic hydrocarbons.
12. Hydrogenation and dehydrogenation of hydrocarbons.
13. Methanization.
14. Oxidation, more particularly of internal combustion engine exhausts.
15. Dehydration of oxygen-containing aliphatic compounds.
16. Conversion of olefins into high-octane fuel products.

A few examples will now be reported in order to illustrate the invention in more detail without, however, limiting the scope of this invention in any way.

EXAMPLE 1

This example is illustrative of the preparation of the porous crystalline silica initialled TRS-27 in the crystalline lattice of which beryllium has been introduced as a replacement for silicon.

In a Pyrex glass vessel constantly maintained in a nitrogen atmosphere there are introduced 40 g (grams) of tetraethyl orthosilicate (TEOS) which are heated with stirring up to a temperature of 80° C. Subsequently, there are added 100 mls of a 20% aqueous solution of tetrapropylammonium hydroxide (% is by wt) and the mixture is maintained stirred and heated until it becomes homogeneous and clear, that which takes roughly one hour. At this stage, there are added 4 g of $Be(NO_3)_2.4H_2O$, dissolved in 80 mls of ethanol. A white precipitate is quickly formed and this is heated, still with stirring, to a boil, so as to dispel all the ethanol, i.e. both the one which has been added and the one which has been formed by the hydrolysis.

The preparation is made up to 150 mls with dist. water, whereafter the Pyrex-glass vessel is introduced in an autoclave and a temperature of 155° C. is maintained for 17 days therein. Upon cooling, the solid which is formed is centrifuged at 10,000 rpm (revolutions per minute) and the cake is slurried in dist. water again and centrifugation is effected once more: this washing run is repeated four times. The product is oven-dried at 120° C. and it is ascertained that it is X-ray crystalline.

In order that the alkaline impurities which are contained in the compound may completely be destroyed, calcination for 16 hours at 550° C. in an airstream can be resorted to, whereafter the solid is repeatedly washed with boiling dist. water containing ammonium acetate in solution therein. Finally, calcination at 550° C. for 6 hours is carried out.

The chemical analysis on a sample thus obtained gives the following composition:

$SiO_2$, 92.7% by wt;
BeO, 3.2% by wt;
$Na_2O$, 0.02% by wt.
Weight loss on calcination at 1100° C.: 4.1%, by wt.
The molar ratio $SiO_2$:BeO in the sample is 12.
The X-ray diffraction spectrum is reported on FIG. 1.
The concentration of $H^+$ ions is $1.5 \times 10^{-3}$ meq per gram and the specific surface area is 400 m$^2$/g.

EXAMPLE 2

This example is illustrative of the preparation of the crystalline silica initialled TRS-28, in the crystalline lattice of which chromium has been introduced as a modifying agent.

In a Pyrex-glass vessel kept in a nitrogen atmosphere, there are placed 40 g of tetraethyl orthosilicate (TEOS) and these are heated with stirring to a temperature of 80° C.

There are added 20 g of a 20% aqueous solution of tetrapropylammonium hydroxide and the mixture is still kept, with stirring, at 80° C. until the mixture itself becomes clear, that which takes roughly one hour.

At this stage, there are added 4 g of $Cr(NO_3)_3.9H_2O$, dissolved in 50 mls of anhydrous methanol.

A compact, pale green gel is formed nearly immediately, to which 0.25 g of KOH dissolved in 20 mls of water, are added, and, still with stirring, the mixture is brought to a boil in order that hydrolysis may be completed and both the ethanol which has been added and that which has been formed by hydrolysis may be driven off by vaporization. The time taken by the latter step is from 2 to 3 hours: the gel is slowly and gradually converted into a pale green powder which is the precursor of the chromium-modified crystalline silica.

The mixture is made up to 150 mls with dist. water and the vessel is placed in an autoclave at the temperature of 155° C. for 13 days.

Upon cooling the autoclave, the solid which has been formed is centrifuged at 5,000 rpm for 15 minutes, the cake is washed 4 times by reslurrying in dist. water and is then dried at 120° C.

The product thus obtained is X-ray crystalline.

In order that the alkaline impurities retained in the compound may be completely destroyed, it is possible to fire at 550° C. for 16 hours in an air stream, whereafter the solid is repeatedly washed by reslurrying it in boiling dist. water which contains, in solution therein, ammonium acetate. The final step is firing (calcination) at 550° C. for 6 hours.

The chemical analysis on the sample thus obtained gives the composition reported below:

% by wt of $SiO_2$, 90.5; % by wt of $Cr_2O_3$, 6.0.
Loss on firing at 1100° C.: 3.5% by wt.
The molar ratio $SiO_2$:$Cr_2O_3$ in the sample is 38.
The material is X-ray crystalline.
The X-ray diffraction spectrum is plotted in FIG. 2.
The concentration of protonic milliequivalents per gram of product is $5.8 \times 10^{-3}$ meq $H^+$ and the specific surface area is 380 m$^2$/g.

EXAMPLE 3

This example is illustrative of the preparation of the porous crystalline silica initialled TRS-66, in the crystalline lattice of which zinc has been introduced as a replacing element.

In a Pyrex-glass vessel kept in an atmosphere which is $CO_2$-free there are introduced 40 g of tetraethyl orthosilicate and there is added a solution of 4 g of $Zn(NO_3)_2.H_2O$ in 40 mls ethanol (95%), with stirring.

There is now added a solution of 20 g of tetrapropylammonium hydroxide, still with stirring, and starting heating until a homogeneous and compact gel is formed.

The gel is crushed and water is added, in which 2 g of KBr have been dissolved, so as to obtain a slurry which is heated with stirring until all the ethanol which is present (the one which has been introduced and that which has been formed by hydrolysis) has been evaporated off. The final preparation is made up to 150 mls with dist. water and transferred to a Pyrex-glass vessel which is then placed in an autoclave and held therein at a temperature of 197° C. for 6 days.

Upon cooling, the solid which has been formed is collected on a filter, washed until the basic reaction is fully discharged, and dried at 120° C.: it is seen that the product is X-ray crystalline.

In order that the residual alkaline impurities in the compound may completely be destroyed, it is possible to fire at 550° C. for 16 hours in an air stream and subsequently to wash the compound repeatedly with boiling dist. water in which ammonium acetate has been dissolved, whereafter the solid is fired at 550° C. for 6 hours.

The chemical analysis of the thusly obtained sample is the following:

$SiO_2$, 88.3% by wt; ZnO, 8.0% by wt; $K_2O$, 0.02% by wt.

Loss on firing at 1100° C.: 3.7% by wt.
The molar ratio $SiO_2$ to ZnO in the sample is 15.0.

The concentration of $H^+$ ions is $2.2 \times 10^{-5}$ meq per gram and the specific surface area, determined with the BET method, is 380 $m^2/g$. BET stands for Brunauer Emmett Teller.

EXAMPLE 4

This example is illustrative of the preparation of the crystalline silica initialled TRS-42, in the crystalline lattice of which beryllium has been introduced as a modifying element.

The procedure of Example 1 hereof is adopted, and 83 g of tetraethyl orthosilicate, 59.6 g of triethanolamine and 1.1 g of $Be(NO_3)_2.4H_2O$ and 2 g of NaOH are used.

The end product is made up to 200 mls with dist. water and is kept in an autoclave at 200° C. for 6 days.

The product, dried at 120° C. is X-ray crystalline.
The chemical analysis of the product fired at 550° C. gives the following data:

$SiO_2$ 96.0% by wt; BeO, 0.4%; $Na_2O$, 0.03%.
Loss on firing at 1100° C.: 3.5% by wt.
The molar ratio $SiO_2$:BeO is 100.

The concentration of $H^+$ ions is $1.2 \times 10^{-3}$ meq/g and the specific surface area determined with the BET method is 380 $m^2/g$.

EXAMPLE 5

This example is illustrative of the preparation of the porous crystalline silica initialled TRS-45 in the crystalline lattice of which boron has been introduced as the modifying agent.

The procedure is that of Example 1 hereof, by reacting 30.5 g of tetramethyl orthosilicate, 14.6 g of triethyl borate and 60 mls of water, the mixture being boiled during one hour. There are now added 6 g of tetrapropylammonium hydroxide.

A gel is formed at once, and is crushed and slurried in water until obtaining a slurry to which 2 g of KOH are added.

After having stirred for 20 hours the boiling slurry, the latter is introduced in an autoclave at 175° C. and held therein for six days.

The product dried at 120° C. is X-ray crystalline. The product, fired at 550° C. gives the following chemical composition:

$SiO_2$, 74.9% by wt; $B_2O_3$, 21.3%; $K_2O$, 0.02%.
Loss on firing at 1100° C.: 3.8% by wt.
The molar ratio $SiO_2$:$B_2O_3$ is 4.
The specific surface area determined with the BET method is 410 $m^2/g$.

EXAMPLE 6

This example is illustrative of the preparation of the porous crystalline silica initialled TRS-64, in the crystalline lattice of which titanium has been introduced as the modifyer.

With the same procedure as in Example 1 hereof, 40 g of tetraethyl orthosilicate, 10 g of tetraethyl orthotitanate (separately hydrolyzed with water and digested in 100 mls of $H_2O_2$ (30% conc.) until forming a clear yellow-orange solution), 20 g of tetrapropylammonium hydroxide (10% aq.soln.) and 2 g of KBr are caused to react. The mixture is maintained in an autoclave at 145° C. for 10 days. The product, dried at 120° C., is X-ray crystalline. The product, upon firing at 550° C. gives the following chemical analysis:

$SiO_2$, 66.5K by wt; $TiO_2$, 29.5%; $K_2O$, 0.02%.
Loss on fire at 1100° C. 3.9% by wt.
The molar ratio $SiO_2$:$TiO_2$ is 3. The specific surface area determined with the BET method is 430 $m^2/g$.

EXAMPLE 7

This example is illustrative of the preparation of the porous crystalline silica initialled TRS-48 in the crystalline lattice of which vanadium has been introduced as the modifying element.

The procedure is as in Example 1 hereof, by reacting 8 g of $NH_4VO_3$ with 200 mls of water containing 20 g of tetrapropylammonium hydroxide, heating until complete dissolution is achieved. There are now added 88 g of tetramethyl orthosilicate and the gel thus obtained is slurried in Water and the slurry is boiled for several hours.

On addition of 0.25 g of KOH, the mixture is placed in autoclave and held therein at 175° C. for six days.

The product, dried at 120° C., is X-ray crystalline. The chemical analysis on the fired product (550° C.) gives the following data:

$SiO_2$, 81.7% by wt; $V_2O_5$, 14.6%; $K_2O$, 0.01%.
Loss on fire at 1100° C.: 3.7% by wt.
The molar ratio $SiO_2$:$V_2O_5$ is 17. The specific surface area determined with the BET method is 410 $m^2/g$.

EXAMPLE 8

This example is illustrative of the preparation of the porous crystalline silica initialled TRS-41, in the crystalline lattice of which beryllium has been introduced as a replacement agent.

The procedure is the same as in Example 1 hereof, by using 38 g of 30%-silica-sol instead of tetraethyl-orthosilicate, the other reactants being left unchanged, under the same working conditions.

The as-obtained product, fired at 120° C. is X-ray crystalline.

The chemical analysis of the product fired at 550° C. gives the following results:

$SiO_2$, 93.1% by wt; BeO, 3.2%; $K_2O$, 0.02%.
Loss on fire, at 1100° C.: 3.7% by wt.
The molar ratio $SiO_2$/BeO is 12.

The properties of this material are identical with those of the product of Example 1 hereof.

EXAMPLE 9

A catalyst initialled TRS-28 is used in the alkylation of benzene with ethylene. 1 ml of the catalyst prepared according to Example 2 hereof is employed in the reaction of alkylation of benzene with ethylene, in a fixed-bed reactor.

The working conditions which have been adopted are as follows:

(A) LHSV=14 (LHSV is the Liquid Hourly Space Velocity)
  Molar ratio benzene:ethylene=7.5;
  Temperature: 440° C.;
  Pressure: 20 kg/$cm^2$ (kilogram per square centimeter).
(B) LHSV is now 2
  Molar ratio benzene:ethylene=7.5;
  Temperature: 400° C.;
  Pressure: 40 kg/$cm^2$.

Figure 3:
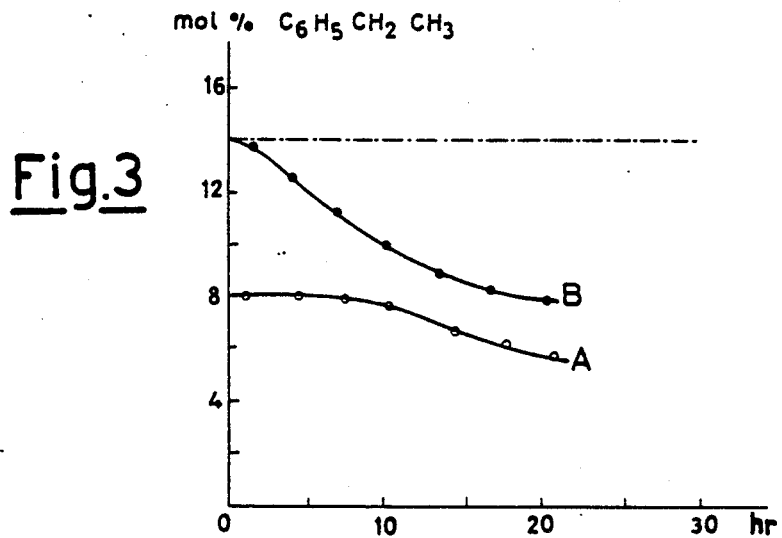
FIG. 3 is a graph that reports the results of tests that were carried out by the use of material of Example 2 in the alkylation of benzene.

The effluents are gaschromatographically analyzed and FIG. 3 of the drawings reports the trend of the A) and the B) tests.

The molar % of ethylbenzene is reported as a function of the reaction time, in hours. The dash-and-dot line corresponds to a 100% conversion of ethylene.

EXAMPLE 10

Catalyst initialled TRS-28, used in the alkylation of benzene with ethanol. 1 ml of catalyst prepared according to Example 2 hereof, is employed in the reaction of alkylation of benzene with ethanol in a fixed-bed reactor.

The working conditions which have been adopted are as follows:
LHSV=10;
Molar ratio $C_6H_6/C_2H_5OH=5$;
Temperature 440° C.—Pressure 20 kg/cm$^2$;
The effluents are analyzed gaschromatographically.

Figure 4:
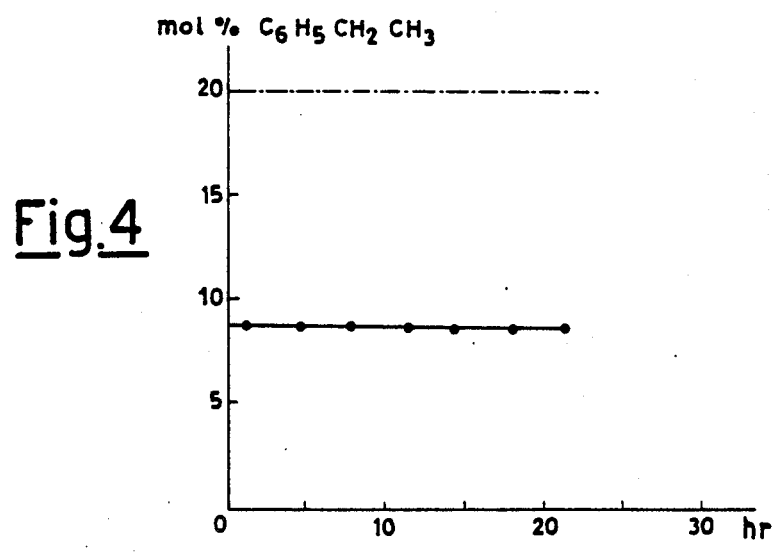
FIG. 4 is a graph that reports the results of tests wherein benzene was alkylated with ethanol.

FIG. 4 of the drawings shows the trend of the reaction and the ordinates report the molar % of ethylbenzene which is present in the reaction products as a function of the reaction time (hours on the abscissae). The dash-and-dot line corresponds to a 100% conversion of ethanol.

Another aspect of the present invention relates to synthetic materials comprised of oxides of silicon and boron, having a porous crystalline structure, the method for their preparation and their practical uses. There are known in the literature natural compact borosilicates, that is non-porous materials, in which boron can have either planar or tetrahedral coordination. Also porous glasses are known, which are obtained by chemically attacking vitreous materials: these, consistently with their origin, may contain silica, alkalies, alumina and also $B_2O_3$. The literature teaches that the incorporation of boron is zeolite-like structures, that is, crystalline structures having a regular porosity, has not been achieved heretofore (Breck, Zeolite Molecular Sieves, J. Wiley and Sons, New York, 1974, page 322).

What is known is only the impregnation, with boric acid, of zeolites which are composed by oxides of aluminum and silicon, as claimed by Kaeding in the U.S. patent specification No. 4,049,573. In this case boron does not enter to become an integral part of the crystalline lattice.

In the foregoing, a crystalline silica has been disclosed, which is modified by elements which enter into the crystalline lattice in replacement for silicon.

Among the replacement elements indicated in the foregoing, also boron has been reported, and in Example 5 hereof the preparation has been illustrated of silica which has been modified with boron.

It has been found, furthermore, that boron, in addition to being a replacing element for silicon, is capable of forming novel materials having a crystalline structure which is porous and is well defined and is akin to the zeolite structure.

These latter materials, which will be called in the following portion of this specification "boralites" for convenient reference and for brevity, can be represented, in their anhydrous state, by the following empyrical formula:

wherein R is the product originated by the organic base used for the formation of the boralites, C is a cation such as H$^+$, NH$_4^+$ or a metallic cation having the valency n, x is equal to or grater than 4 and preferably tends to higher values, up to 1,000, these values being different for each type of boralite, an improved thermal stability being connected with the high ratios $SiO_2/B_2O_3$.

It should be observed that R$_2$O is absent, particularly but not exclusively, after that the boralite concerned has been subjected to calcination (firing).

Out of the boralites corresponding to the general formula reported above, there have been synthesized, in particular, four different types, which will be called Boralite A, Boralite B, Boralite C and Boralite D, for ready reference purposes, which possess a definite crystalline structure and the X-ray diffraction spectra relative to the H$^+$ forms calcined at high temperatures (450° C. to 750° C.) exhibit the significant lines reported in the Tables from I to IV hereof.

The presence of other cations in the stead of H$^+$ causes minor variations in the spectra, in a manner which is akin to that of the conventional zeolites.

The Infrared (IR) spectra exhibit a characteristic band which is a function of the quantity of boron which has been introduced and which is comprised between 910 and 925 cm$^{-1}$.

The method for the preparation of the boralites is based on the reaction, under hydrothermal conditions, of a derivative of silicon, a derivative of boron, and an appropriate chelating agent, preferably an alkylonium compound, at a pH comprised between 9 and 14, at a temperature comprised between 100° C. and 220° C. and for a time variable between 1 and 30 days.

High-purity boralites can be obtained with the use of organic derivatives of boron and silicon, such as trialkyl borates and tetraalkyl orthosilicates and by carrying out the hydrothermal process in Teflon (R.T.M.) vessels, or in vessels of polypropylene, platinum and others in order to make sure that the alkaline solution may not extract impurities from the crystallization vessel.

The absence of impurities guarantees for the boralites special properties such as hydrophobic character and the resultant lack of dehydrating power.

If a very high purity is not a must, there can be used cheaper sources for the components, such as, for boron, boric acid, sodium borate and borax, and, for silicon, colloidal silica, silica-gel, sodium silicate, aerosil and others, and, for the crystrallization, vessels of glass, stainless steel and others can be used.

In such cases, the boralites can contain impurities coming from the reactants or the crystallization vessels: thus, for example, commercial silicas contain up to 2,000 ppm (parts per million) of Al$_2$O$_3$, but it has been ascertained that percentages as high as 10,000 ppm of Al$_2$O$_3$ do not alter the structural and crystallographic properties, even though, obviously, other properties are modified, such as the hydrophobic character and the dehydrating power.

As the chelation agents, compounds can be used having amine, ketone, alcoholic, acidic function and other functions, but, more frequently than all, alkylonium bases are used, such as tetraalkylammonium hydroxides. The selection of such compounds, together with the selection of the reactants, has a determining bearing to the end of the formation of the boralites.

Mineralizing agents can be added, such as alkali metal- or alkaline earth metal hydroxides or halides.

Boralite A can be characterized, in terms of molar ratios of the oxides and in the anhydrous condition, by the formula:

wherein R is the tetramethylammonium (TMA) cation, C can be H+, NH4+, or a metallic cation having the valency n.

The material which can be obtained by calcination of the boralite A has the X-ray diffraction spectrum in the H+ form as regards the most significant lines, as reported in Table 1.

Boralite B can be characterized, in terms of molar ratio of the oxides and in the anhydrous state, by the formula:

$$(0-1)R_2O:(0-1)C_{2/n}O:B_2O_3:(5-50)SiO_2$$

wherein R is the tetraethylammonium cation (TEA), C can be H+, NH4+, or a metallic cation having the valency n.

The material which can be obtained by calcination of the boralite B, has the X-ray diffraction spectrum in the H+ form, as reported in Table II, as regards the most significant lines.

Boralite C can be characterized, in terms of molar ratio of the oxides and in the anhydrous state, by the formula:

$$(0-1)R_2O:(0-1)C_{2/n}O:B_2O_3:(4-1,000)SiO_2$$

wherein R is a tetraethylammonium or a tetrapropylammonium cation or a nitrogen-containing cation derived from an amine, such as ethylene diamine, C can be H+, NH4+, or a metallic cation having the valency n.

The boron-modified silica of Example 5 hereof is a boralite C. The material which can be obtained by calcination of the boralite C is characterized, in the H+ form, by the X-ray diffraction spectrum reported in Table III as far as the most significant lines are concerned.

Boralite D can be characterized, in terms of molar ratios of the oxides and in the anhydrous condition, by the formula:

$$(0-1)R_2O:(0-1)C_{2/n}O:B_2O_3:(4-20)SiO_2$$

wherein R is a tetrabutylammonium cation, C is H+, NH4+ or a metallic cation having the valency n.

The material which can be obtained by calcination of the boralite D is characterized, in the H+ form, by the X-ray diffraction spectrum reported in TABLE IV as regards the most significant lines.

The boralites are very stable both in the thermal treatments at high temperatures and the thermal treatments in the presence of water vapor.

The boralites, and more particularly the A-, B-, C- and D-boralites, exemplified above, can be used for catalytic reactions or for absorption processes, as such or dispersed on a more or less inert supporting body to be selected, preferably, from among silicas, aluminas and clay-like materials, and can be find application in a large number of reactions, such as those exemplified in the foregoing.

A further set of examples will now be set forth, in order to illustrate without limitation a few further examples, which are more particularly concerned with the second aspect of this invention.

EXAMPLE 11

This example is illustrative of the preparations of the boralite A.

A Pyrex-glass vessel maintained in a CO2-free atmosphere is charged with 132 g of a 25% aqueous solution of tetramethylammonium hydroxide (concentration in by wt) to which 18.6 g of boric acid are added with stirring.

On completion of the dissolution there are added, still with stirring, 187.5 of tetraethylorthosilicate.

The reaction mixture is heated, still with stirring, to 60° C. and a white lactescent precipitate is gradually formed, while ethanol produced by hydrolysis of ethyl silicate is concurrently driven off.

After 12 hours, the alcohol has been entirely eliminated and there are added 0.18 g of KOH and dist. water until making up to an overall volume of about 300 mls. At this stage, the reaction mixture is transferred to a Reflon-lined static autoclave and the hydrothermal treatment at 145° C. is started, to be continued for a time of twelve days. The as-obtained product is then allowed to cool to room temperature, collected on a filter, carefully washed with dist. water and dried at 120° C.

The product is composed by crystals with a grit size comprised between 0.1 and 0.5 micron approximately.

A portion of the sample is calcined at 750° C.

The product is characterized by a molar ratio $SiO_2:B_2O_3=11$. The X-ray diffraction spectrum of the H+ form corresponds to the data of Table I.

The IR-spectrum exhibits a characteristic band for boron which cannot be seen in the conventional zeolites, at 921 cm$^{-1}$.

EXAMPLE 12

This example illustrates the preparation of the boralite A by using colloidal silica.

With the same procedure and in the same order as disclosed in Example 11, there are placed in the Pyrex-glass vessel 210 g of a 25% (by wt) solution of tetramethylammonium hydroxide, 27 g of $H_3BO_3$ and 240 g of Ludox colloidal silica (conc. 40%).

Upon stirring and heating to 80° C. for one hour, the reaction mixture is placed in a titanium autoclave having 1-liter volume and fitted with stirring mechanisms and the hydrothermal treatment at 150° C. is carried out during 10 days under the pressure which is spontaneously generated.

The crystalline product of the reaction is collected on a filter, washed and dried and fired at 750° C. for 6 hours: it exhibits, in the H+ form, the X-ray diffraction spectrum reported in Table I and an IR band at 917 cm$^{-1}$.

In addition, the product displays the following properties:

Actual density (helium method): 2.19 g/cm$^3$ (grams/cubic centimeter),
Acidity (CsCl method): pH 2.4,
$SiO_2:B_2O_3=12.3$.

EXAMPLE 13

This example illustrates the preparation of the porous synthetic crystalline Boralite of the B type.

Under the conditions of Example 12 hereof, there are reacted 110 g of a 25% (by wt) solution of tetraethylammonium hydroxide, 12 g of boric acid and 100 g of the 40%-Ludox A.S. colloidal silica.

The hydrothermal treatment is carried out for 9 days at 150° C. in a 300-ml, Teflon-lined static autoclave.

The crystalline product which is obtained upon filtration washing, drying and firing is composed by spherulitic particles having an average diameter of 1.3 micron.

The chemical analysis gives the molar ratio $SiO_2:B_2O_3$ of 6.86. The X-ray spectrum in the $H^+$ form calcined at 550° C. corresponds to the data of Table II. The IR-spectrum exhibits a characteristic band at 921 $cm^{-1}$.

The specific surface area, determined with nitrogen according to the BET method is 421 $m^2/g$.

The volume of the pores is 0.18 $cm^3/g$ (cubic centimeter per gram). The actual density (helium method) is 2.32 $g/cm^3$. The acidity, as measured with the CsCl method is pH 1.8.

EXAMPLE 14

This example is for illustration of the preparation of boralite C. The procedure is as in Example 11, by reacting 90 g of a 25% by wt solution of tetrapropylammonium hydroxide, 37.5 g of boric acid, 125 mls of dist. water and 62.4 g of tetraethyl orthosilicate.

By operating in the autoclave of Example 13 at 160° C. for 11 days and after the usual treatment for obtaining the $H^+$ form, a product is obtained which has an olive-like shape with dimensions of 10–15 microns, the X-ray diffraction spectrum of which corresponds to the tabulations of Table III and has an IR-band at 920 $cm^{-1}$, the $SiO_2:B_2O_3$ molar ratio being 4.

EXAMPLE 15

The same procedure as in the previous example 14 is adopted by reacting, in the order given, 37.5 g of orthoboric acid, 250 mls of water, 3 g of KOH, 180 g of a 25% (by wt) solution of tetrapropylammonium hydroxide, 5 g of KBr, and 124.8 g of tetraethyl orthosilicate.

By operating in the autoclave of Example 12 at 175° C. for 6 days, after the usual treatment for obtaining the $H^+$ form, a spheroidal product is obtained which has an X-ray diffraction spectrum corresponding to that of the boralite C as reported in TABLE III, with an IR-band at 915 $cm^{-1}$ and an $SiO_2:B_2O_3$ molar ratio of 11.2.

Actual density (helium method): 2.36 $g/cm^3$.

Specific surface area (BET method with nitrogen): 377 $m^2/g$. Volume of the pores: 0.18 $cm^3/g$. Pore diameter between 5 and 30 Angstrom units.

EXAMPLE 16

The procedure is the same as in Example 14 by reacting, in the order given, 30 g of tetramethyl orthosilicate, 14.6 g of triethyl borate, 1,100 g of water, 80 g of tetrapropylammonium hydroxide (25% by wt) and 2 g of KOH, crystallizing at 190° C. for 6 days, washing and subsequent operations just as in Example 14.

The X-ray spectrum of the $H^+$ form calcined at 550° C. corresponds to that of Boralite C as reported in Table III. The molar ratio $SiO_2:B_2O_3$ is 17 and the specific surface area, determined with the BET method is 380 $m^2/g$.

EXAMPLE 17

This example illustrates the preparation of boralite C. The procedure is the same as for Example 14, by reacting, in the order given, 130 g of tetraethyl orthosilicate, 15 g of boric acid, 250 mls of water, 70 g of tetrapentylammonium hydroxide in 250 mls water and 5 g of KOH in 50 mls of water.

Stirring is maintained at 60° C.–80° C. for 24 hours and the mixture is introduced in a 1-liter titanium autoclave equipped with a stirrer and is maintained for 12 days at 165° C. The product, calcined at 550° C. exhibits the X-ray diffraction spectrum as reported in Table III for boralite C.

Molar ratio $SiO_2:B_2O_3$:13.9

EXAMPLE 18

This example is for illustrating the preparation of boralite C. The procedure is the same as in Example 14, by reacting 88.7 g of tetraethylammonium hydroxide (20% by wt solution), 4.15 g of $H_3BO_3$, 62.5 g of tetraethyl orthosilicate. From the clear solution which is thus obtained, ethanol is driven off at 60° C.–80° C. without experiencing any formation of gel. The mixture is introduced in a 250-ml stainless steel autoclave and is maintained at 150° C. for 10 days.

Under such conditions, a compact gel is formed, which is slurried into 100 mls of dist. water, to which there are added 2.5 g of KOH and the mixture is heated with stirring to 80° C., water being evaporated off until reaching a volume of 250 mls in total, the operation being possibly repeated until the gel takes a lactescent appearance.

The gel is brought to the autoclave again for 15 days at 175° C., whereafter the sequence of operations is that of Example 14.

The X-ray diffraction spectrum in the form $H^+$, calcined at 550° C. corresponds to the tabulations of Table III for boralite C.

The $SiO_2:B_2O_3$ is 12.1

EXAMPLE 19

This example is an illustration of the preparation of boralite C from ethylene diamine.

By following the procedure of Example 12, there are reacted 4.25 g of NaOH, 120 mls of water, 6 g of $H_3BO_3$, 85 g of ethylene diamine, and 50 g of 40% Ludox A.S. Colloidal silica.

Hydrothermal treatment is performed in a 300-ml, teflon-lined autoclave for 9 days at 175° C.

The X-ray diffraction spectrum, in the form $H^+$ calcined at 550° C., corresponds to the tabulations reported in Table III for boralite C. The $SiO_2:B_2O_3$ molar ratio is 11.3.

EXAMPLE 20

This example is illustrative of the preparation of boralite D. By adopting the same procedure as in Example 11, there are reacted 225 g of a 40% by wt solution of tetrabutylammonium hydroxide, 20 g of boric acid, 200 g of tetraethyl orthosilicate, 0.2 g of KOH and, upon driving off the ethanol, dist. water is added to make up to one one liter.

The hydrothermal treatment is carried out in a titanium autoclave equipped with a stirring device, at 165° C. for 12 days.

The crystalline product, in the $H^+$ form calcined at 550° C., displays the X-ray diffraction spectrum of boralite D, as reported in Table IV. The IR-spectrum shows a band at 919 $cm^{-1}$, which is characteristic of boron. The specific surface area (BET method with nitrogen) is 415 $m^2/g$ and the volume of the pores is 0.18 $cm^3/g$.

The $SiO_2:B_2O_3$ molar ratio is 4.8.

EXAMPLE 21

By adopting the same procedure as in Example 20, there are reacted 113 g of a 40% (by wt) solution of tetrabutylammonium hydroxide, 10 g of boric acid, 75 g of 40% Ludox A.S. colloidal silica.

The hydrothermal treatment is carried out at 150° C. for 12 days in a Teflon-lined autoclave.

The thusly obtained crystalline product has a molar ratio $SiO_2:B_2O_3$ equal to 10.4 and, in the $H^+$ form calcined at 550° C. exhibits the X-ray diffraction spectrum reported in Table IV. The IR-spectrum displays the characteristic 918 $cm^{-1}$ band.

The specific surface area (BET method with nitrogen) is 335 $m^2/g$, and the volume of the pores is 0.155 $cm^3/g$.

EXAMPLE 22

An electrically heated tubular reactor having an inside diameter of 8 mm is charged with 3 mls of the boralite A catalyst as prepared according to Example 11 and having a grit size comprised between 14 and 30 mesh (ASTM, USA series).

Through a metering pump, there is introduced in the reactor a charge of methyl-tert.butyl ether which has been preheated by having it flowing through a preheating tube.

Downstream of the reactor, a pressure-checking valve calibrated to 6 bar is installed, with a properly heated sampling appliance which, upon reduction of the pressure, permits the introduction of the reactor effluent in a gaschromatograph.

By heating to the temperatures reported in Table V, methyl tert.butyl ether is fed with rates of flow of 6 $cm^3$ an hour, that is with an LHSV (Liquid Hourly Space Velocity) of 2, the results being likewise tabulated in Table V.

EXAMPLE 23

The reactor of Example 22 is charged with 3 mls of the boralite B catalyst as prepared according to Example 13, which has a grit size comprised between 30 and 50 mesh (ASTM, USA series). By operating under a pressure of 6 bars as in Example 22, the data tabulated in Table VI are obtained.

EXAMPLE 24

The reactor of Example 22 is charged with 2 mls of the boralite C catalyst as prepared according to Example 14, having a grit size of from 7 and 14 mesh (ASTM, USA series). By operating according to the procedure of Example 22 methyl tert.butyl ether is fed in and the test is continued for a few hours in order to test the constancy of the catalytic activity with the lapse of time.

The operations are carried out in an oven at 150° C. and under a pressure of 6 bar, with an LHSV of 2, the results which have thus been obtained being tabulated in Table VII.

EXAMPLE 25

The reactor described in Example 22 is charged with 3 mls (1.35 g) of boralite D as prepared according to Example 20, having a grit size of from 30 to 50 mesh (ASTM; USA series).

Methyl tert.butyl ether is fed in under the conditions tabulated in Table VIII, the results being likewise tabulated in Table VIII.

TABLE I

BORALITE TYPE A

| Interplanar distances d (Å) | Relative intensity |
|---|---|
| 8.82 | M |
| 8.25 | S |
| 6.52 | M |
| 6.12 | M |
| 5.61 | MW |
| 5.32 | W |
| 4.42 | MW |
| 4.27 | MW |
| 4.09 | MW |
| 4.02 | MW |
| 3.92 | MW |
| 3.83 | M |
| 3.47 | W |
| 3.42 | W |
| 3.27 | MW |
| 2.88 | W |
| 2.74 | W |
| 2.47 | W |

Key to symbols:
VS = very strong
S = strong
MW = Medium weak
W = weak
Slight variations of the values tabulated above can be observed as the molar ratio $SiO_2:B_2O_3$, the firing temperature and the nature of the cation concentrated are varied.

TABLE II

BORALYTE TYPE B

| Interplanar distances d (Å) | Relative intensity |
|---|---|
| 11.23 | S |
| 6.52 | W |
| 5.98 | W |
| 4.08 | MW |
| 3.90 | S |
| 3.46 | MW |
| 3.26 | MW |
| 3.05 | W |
| 2.98 | MW |
| 2.65 | W |
| 2.05 | W |

Key to symbols:
VS = very strong
S = strong
MW = medium weak
W = weak
Slight variations of the values tabulated above can be observed as the molar ratio $SiO_2:B_2O_3$, the firing temperature and the nature of the cation concerned are varied.

TABLE III

BORALITE TYPE C

| Interplanar distances d (Å) | Relative intensity |
|---|---|
| 11.09 | VS |
| 9.94 | S |
| 9.67 | MW |
| 6.66 | W |
| 6.33 | MW |
| 5.96 | MW |
| 5.67 | MW |
| 5.55 | MW |
| 5.33 | W |
| 5.00 | W |
| 4.95 | W |
| 4.58 | W |
| 4.34 | W |
| 4.24 | MW |
| 3.98 | W |
| 3.83 | S |
| 3.80 | S |
| 3.73 | MW |
| 3.70 | M |
| 3.63 | MW |
| 3.46 | W |
| 3.42 | W |
| 3.33 | W |
| 3.29 | W |

TABLE III-continued
BORALITE TYPE C

| Interplanar distances d (Å) | Relative intensity |
|---|---|
| 3.23 | W |
| 3.03 | MW |
| 2.97 | MW |
| 2.93 | W |
| 2.72 | W |
| 2.59 | W |
| 2.48 | W |
| 2.41 | W |
| 2.38 | W |
| 2.00 | MW |
| 1.98 | MW |

Key to symbols:
VS = very strong
S = strong
MW = medium weak
= weak

Slight variations may occur as to the values tabulated above as the molar ratio SiO₂:B₂O₃, the firing temperature and the nature of the cation concerned are varied. Slight variations of the values tabulated above may occur, consistently with the variation of the molar ratio of silica to boric oxide, the variation of the firing temperature and the nature of the cation concerned.

TABLE IV
BORALITE TYPE D

| Interplanar distances d (Å) | Relative Intensity |
|---|---|
| 11.12 | VS |
| 10.00 | S |
| 6.67 | W |
| 6.36 | W |
| 5.97 | M |
| 5.56 | MW |
| 4.99 | MW |
| 4.59 | W |
| 4.34 | W |
| 3.83 | S |
| 3.70 | M |
| 3.62 | W |
| 3.46 | W |
| 3.33 | W |
| 3.04 | W |
| 2.97 | MW |
| 2.50 | W |
| 2.48 | W |
| 2.00 | MW |

Key to symbols:
VS = very strong
S = strong
MW = medium weak
W = weak

Slight variations of the tabulated values may be experienced as the molar ratio of SiO₂ to B₂O₃, the firing temperature and the nature of the cation concerned are varied.

TABLE V
Catalyst:Boralite type A - Pressure:6 bar:LHSV = 2

| Test N° | Oven temperature °C. | Conversion of the methyl tert.butyl ether % | Recovery of methanol % | Recovery of isobutene % |
|---|---|---|---|---|
| 1 | 200 | 14.5 | 99.9 | 99.8 |
| 2 | 225 | 22.7 | 99.9 | 99.8 |
| 3 | 275 | 71.7 | 99.8 | 99.8 |
| 4 | 305 | 99.1 | 99.7 | 99.7 |
| 5 | 315 | 99.9 | 99.7 | 99.7 |

TABLE VI
Catalyst:Boralite type B - pressure 6 bar

| Test N° | Oven temperature °C. | LHSV | Conversion of methyl tert.butyl ether % | Recovery of methanol % | Recovery of isobutene % |
|---|---|---|---|---|---|
| 1 | 160 | 2 | 93.7 | 99.8 | 99.3 |
| 2 | 170 | 2 | 99.3 | 99.1 | 99.0 |
| 3 | 170 | 4 | 98.2 | 99.6 | 99.1 |
| 4 | 150 | 4 | 96.1 | 99.9 | 99.6 |

TABLE VII
Catalyst:Boralite C - pressure:6 bar LHSV = 2 Oven temperature = 150° C.

| Test N° | Time, hours | Conversion of methyl tert.butyl ether % | Recovery of methanol % | Recovery of isobutene % |
|---|---|---|---|---|
| 1 | 1 | 97.6 | 99.7 | 99.4 |
| 2 | 2 | 95.9 | 99.9 | 99.5 |
| 3 | 5 | 96.9 | 99.9 | 99.6 |
| 4 | 24 | 94.5 | 99.9 | 99.6 |
| 5 | 25 | 96.8 | 99.9 | 99.7 |
| 6 | 26 | 95.8 | 99.9 | 99.7 |

TABLE VIII
Catalyst:Boralite D - Pressure = 6 bar

| Test N° | Oven temperature °C. | LHSV | Conversion of methyl tert.butyl ether % | Recovery of methanol % | Recovery of isobutene % |
|---|---|---|---|---|---|
| 1 | 136 | 2 | 96.3 | 99.9 | 99.9 |
| 2 | 136 | 4 | 75.3 | 99.9 | 99.9 |
| 3 | 150 | 4 | 96.5 | 99.9 | 99.8 |

We claim:
1. A synthetic, silica-based crystalline material consisting essentially of crystalline silica modified through the introduction of boron into the crystalline latice as a replacement element for silicon said material being represented by the general formula:

$$aR_2O \cdot bC_{2/n}O \cdot B_2O_3 XSiO_2$$

wherein R is tetramethylammonium; C is a cation selected from the group consisting of $H^+$ and $NH_4^+$ or metal having a valence equal to n; a is 0–1; b is 0–1; x is a number from 8–30 said silica based crystalline material having the following X-ray diffraction lines and relative intensity;

| d (A) | Relative Intensity |
|---|---|
| 8.82 | M |
| 8.25 | S |
| 6.52 | M |
| 6.12 | M |
| 5.61 | MW |
| 5.32 | W |
| 4.42 | MW |
| 4.27 | MW |
| 4.09 | MW |
| 4.02 | MW |
| 3.92 | MW |
| 3.83 | M |
| 3.47 | W |
| 3.42 | W |
| 3.27 | MW |
| 2.88 | W |
| 2.74 | W |
| 2.47 | W. |

2. A synthetic, silica based crystalline material consisting essentially of crystalline silica modified through the introduction of boron into the crystalline latice as a replacement element for silicon said material being represented by the general formula:

$$aR_2O \cdot bC_{2/n}O \cdot B_2O_3 XSiO_2$$

wherein R is tetraethylammonium; C is a cation selected from the group consisting of $H^+$ and $NH4^+$ or a metal having a valence equal to n; a is 0–1; b is 0–1; x is a number from 5–50 having the following x-diffraction lines and relative intensity;

| d(A) | Relative Intensity |
|---|---|
| 11.23 | S |
| 6.52 | W |
| 5.98 | W |
| 4.08 | MW |
| 3.90 | S |
| 3.46 | MW |
| 3.26 | MW |
| 3.05 | W |
| 2.98 | MW |
| 2.65 | W |
| 2.05 | W. |

3. A method for preparing a synthetic, silica-based boron modified material selected from the group consisting of crystalline silica modified through the introduction of boron into the crystalline latice as a replacement element for silicon said material being represented by the general formula:

$$aR_2O \cdot bC_{2/n}O \cdot B_2O_3 XSiO_2$$

wherein R is tetramethylammonium; C is a cation selected from the group consisting of $H^+$ and $NH_4^+$ or a metal having a valence equal to n; a is 0–1; b is 0–1; x is a number from 8–30 said silica based crystalline material having the following x-ray diffraction lines and relative intensity;

| d (A) | Relative Intensity |
|---|---|
| 8.82 | M |
| 8.25 | S |
| 6.52 | M |
| 6.12 | M |
| 5.61 | MW |
| 5.32 | W |
| 4.42 | MW |
| 4.27 | MW |
| 4.09 | MW |
| 4.02 | MW |
| 3.92 | MW |
| 3.83 | M |
| 3.47 | W |
| 3.42 | W |
| 3.27 | MW |
| 2.88 | W |
| 2.74 | W |
| 2.47 | W. | or by the general formula:

$$aR_2O \cdot bC_{2/n}O \cdot B_2O_3 XSiO_2$$

wherein R is tetraethylammonium; C is a cation selected from the group consisting of $H+$ and $NH4+$ or a metal having a valence equal to n; a is 0–1; b is 0–1; x is a number from 5–50 having the following x-diffraction lines and relative intensity;

| d(A) | Relative Intensity |
|---|---|
| 11.23 | S |
| 6.52 | W |
| 5.98 | W |
| 4.08 | MW |
| 3.90 | S |
| 3.46 | MW |
| 3.26 | MW |
| 3.05 | W |
| 2.98 | MW |
| 2.65 | W |
| 2.05 | W. | said method characterized in that it comprises the steps of reacting, in an aqueous, alcoholic, or hydroalcoholic solution, a derivative of silicon and a derivative of a modifying element selected from the group consisting of the oxides, hydroxides, alkoxy derivatives, salts, and halides of boron with a substance having a clathrating effect that is selected from the group consisting of tetramethylammonium hydroxide and tetraethylammonium, hydroxide, adding one or more mineralizing agents selected from the group consisting of the alkaline metal hydroxides and halides in order to encourage crystalization and crystalizing the mixture in an enclosure for a period of from a few hours to a number of days at a temperature of 145°–150°, cooling the mixture and, upon collection on a filter and thereafter washing, drying and firing in air the resultant composition at a temperature between 300° C. and 700° for a time of from 2 hours to 24 hours, washing with distilled water brought to a boil and containing dissolved therein an ammonium salt, and finally firing again at the same temperature and for the same time specified above.

4. A method as defined in claim 3 wherein tetramethylammonium hydroxide is employed and a temperature of 150° is employed.

5. A method as defined in claim 3 wherein tetraethylammonium hydroxide is employed and a temperature of 145°–150° C. is employed.

6. A method according to claim 3 wherein the derivative of silicon is selected from the group consisting of silica-gels.

7. The product produced by the process of claim 3.

* * * * *